(12) United States Patent
Shiue

(10) Patent No.: US 7,100,215 B2
(45) Date of Patent: Sep. 5, 2006

(54) GOGGLES WITH CHANGEABLE LENSES

(75) Inventor: Chih-Cheng Shiue, Escondido, CA (US)

(73) Assignee: QDS Injection Molding LLC, Escondido, CA (US)

( * ) Notice: Subject to any disclaimer, the term of this patent is extended or adjusted under 35 U.S.C. 154(b) by 45 days.

(21) Appl. No.: 10/920,263

(22) Filed: Aug. 18, 2004

(65) Prior Publication Data
US 2006/0048289 A1 Mar. 9, 2006

(51) Int. Cl.
*A61F 9/02* (2006.01)
(52) U.S. Cl. ................ 2/443; 2/448; 351/116
(58) Field of Classification Search .............. 2/443, 2/448, 452, 424, 428; 351/116, 43
See application file for complete search history.

(56) References Cited
U.S. PATENT DOCUMENTS 6,405,384 B1 * 6/2002 Chiang .................. 2/428
6,532,603 B1 * 3/2003 Lan ...................... 2/428
6,865,753 B1 * 3/2005 Nishida ................. 2/426
6,908,194 B1 * 6/2005 Johnson ............... 351/156
2003/0037367 A1 * 2/2003 Fukasawa ............... 2/428
2005/0036103 A1 * 2/2005 Bloch .................. 351/116

* cited by examiner

Primary Examiner—Katherine Moran
(74) Attorney, Agent, or Firm—Troxell Law Office, PLLC

(57) ABSTRACT

A pair of goggles having a main frame including two fitting members, two lenses fitted in the main frame, two hollow side guards, and a band secured to the side guards. Each of the two fitting members being separable at a line extended from an inner edge of a lens opening in the main frame to an outer edge of the main frame and having two latches extending rearwardly from the two fitting members. Inserting the latch into the side guard will fasten the main frame and the side guard together. Pressing and pulling the latch out of the side guard will disengage the main frame from the side guard. Pulling both latches away from each other will separate each of the two fitting members allowing the lens to be changed. Another embodiment includes a flexible second frame. The lenses are fitted in both the flexible second frame and the main frame.

4 Claims, 3 Drawing Sheets

GOGGLES WITH CHANGEABLE LENSES

FIELD OF THE INVENTION

The present invention relates to goggles and more particularly to a pair of goggles having separable fitting members for changing the lenses.

BACKGROUND OF THE INVENTION

It is known that lenses of a conventional pair of goggles may become scratched or worn. Also, the lenses are fixedly connected within a frame. Typically, once the lenses become scratched or worn the goggles are discarded, which is not economical.

Some types of goggles have incorporated an arrangement for changing the lenses so that the goggles can be used for multiple purposes. For example, they can be used as safety goggles, swimming goggles, ski goggles, or the like. These types of goggles are classified as one of two types. The first type has one or two lenses fitted in a flexible frame. However, so far as the present inventor is aware, it has had no market acceptance. The second type has one or two lenses fitted in a hard frame and fastened by a fastening device. However, these types of goggles still have many drawbacks.

SUMMARY OF THE INVENTION

It is an object of the present invention to provide a pair of goggles including a main frame, two lenses fitted in the main frame; two hollow side guards; and a band secured to the side guards. The main frame has two fitting members and two latches extended rearward from the fitting members. Each of the two fitting members are separable at a line that extends from an inner edge of each of the two lens openings of the main frame to an outer edge of the main frame. When the latch is inserted into the side guard, the main frame and the side guard will be fastened together. By pressing and pulling the latches out, the side guard will disengage from the main frame. The lenses can be changed by pulling opposite sides of the fitting members away from each other to enlarge the lens openings.

In one embodiment of the present invention, each of the two latches has an upper and a lower latched member, and the side guard includes a hollow forward member having a forward opening, two side openings, an outer opening, and a rear opening. Each of the two side guards includes a rear member having a slot to which an end of the band are connected, and a flexible forward projection adapted to be inserted into the rear opening of the hollow forward member and project from the outer opening thereby fastening the forward and rear members together. Inserting the latched members into the front opening such that the latched members project from the side openings will fasten the main frame and the side guard together. Pressing and pulling the latched members out of the side openings and the forward opening will disengage the main frame from the side guard. Pulling the latched members away from each other will separate the fitting members and enlarge each of the lens openings so that the lenses can be changed.

In a second embodiment of the present invention, the goggles include a flexible second frame. The flexible second frame and the main frame are connected together with the lenses.

The above and other objects, features and advantages of the present invention will become apparent from the following detailed description taken with the accompanying drawings.

DETAILED DESCRIPTION OF THE PREFERRED EMBODIMENTS

Figure 1:
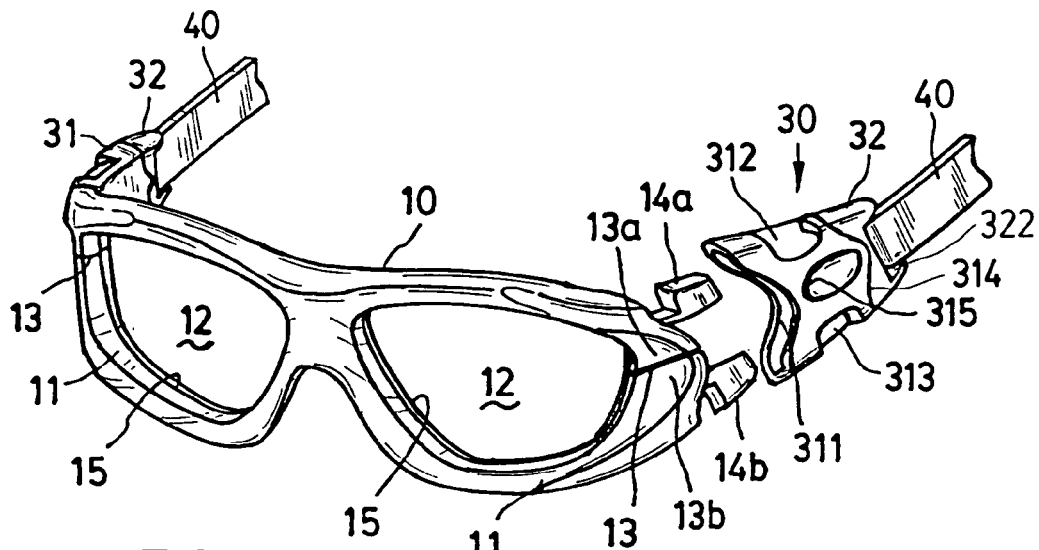
FIG. 1 is an exploded perspective view of a first embodiment of the goggles according to the present invention.
Figure 2:
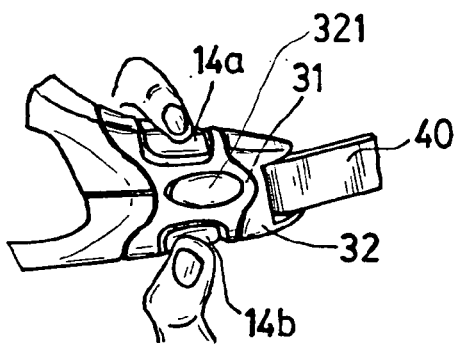
FIG. 2 is an enlarged perspective view illustrating the endpiece and the side guard of FIG. 1.
Figure 3:
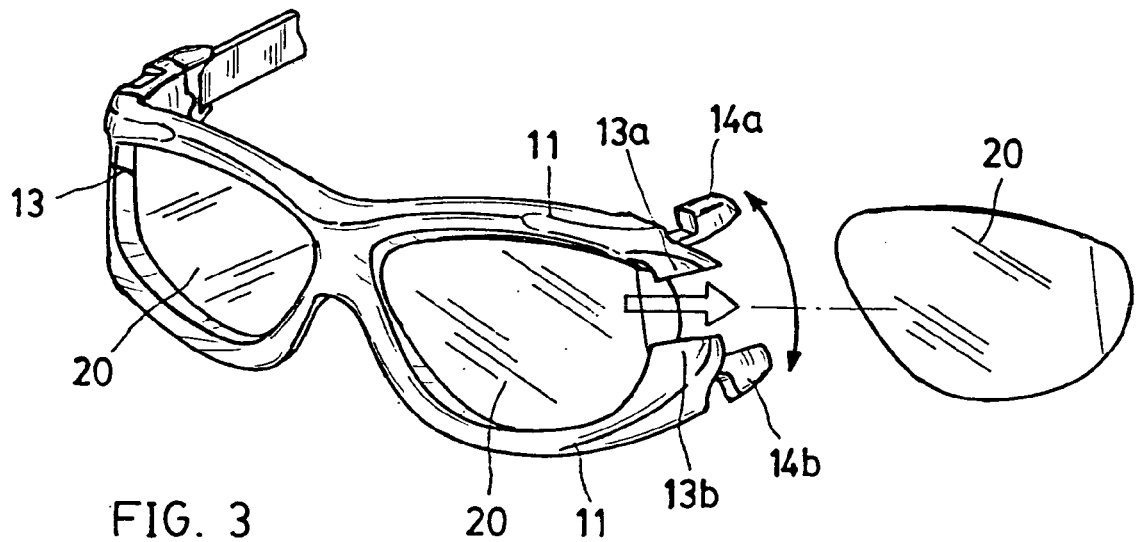
FIG. 3 is an exploded view illustrating removal of lens.

FIGS. 1–3 show a pair of goggles constructed in accordance with a first embodiment of the invention that includes a main frame 10, two lenses 20, two side guards 30, and a band 40.

The main frame 10 includes two fitting members 11 located on opposing sides of the main frame 10. Each of the two fitting members 11 are separable on an outer end at a separation line 13 and have an upper member 13a and a lower member 13b formed on opposite sides of the separation line 13. The main frame 10 includes two lens openings 12. Each of the two lens openings 12 is located on an interior opening in one of the two fitting members 11 and includes a groove 15. Each of the two fitting members 11 includes a pair of upper and lower latched members 14a and 14b in which the upper latched member 14a extends rearwardly from the upper member 13a and the lower latched member 14b extends rearwardly from the lower latched member 13b. One of the two lenses 20 is fitted into each of the two lens openings 12.

Each of the two side guards 30 includes a hollow forward member 31 and a rear member 32. The hollow forward member 31 includes a front opening 311, two side openings 312 and 313, an outer opening 315, and a rear opening 314. The rear member 32 has a flexible forward projection 321 adapted to be removably inserted into the rear opening 314 and project from the outer opening 315 to fasten the front and the rear members 31 and 32 together.

A band 40 has opposing ends adjustably fastened to a slot 322 of the rear member 32. The band 40 is adjustable to fit the head of a user.

To assemble the main frame 10 and the side guard 30, the latched members 14a and 14b of each of the two fitting members 11 are pressed inwardly toward one another and inserted into the front opening 311 of the hollow forward member 31 of one of the two side guards 30. Once the latched members 14a and 14b align with the side openings 312 and 313, they will press outwardly, and move into and project from the side openings 312 and 313, respectively.

To disassemble the main frame 10 and the side guard 30, the latched members 14a and 14b are pressed inwardly and out of the side openings 312 and 313 until they are within an interior of and can be withdrawn from the forward opening 311 of the hollow forward member 31. As a result, the main frame 10 and the side guard 30 are separated.

When the main frame 10 and the side guard 30 are separated, each of the lenses 20 may be changed by pressing the latched members 14a and 14b away from each other and then removing each of the lenses 20 out of the lens openings 12. New lenses 20 can be inserted into each of the two the lens openings 12 separating the latched members 14a and 14b away from each other and inserting each of the new lenses.

Figure 4:
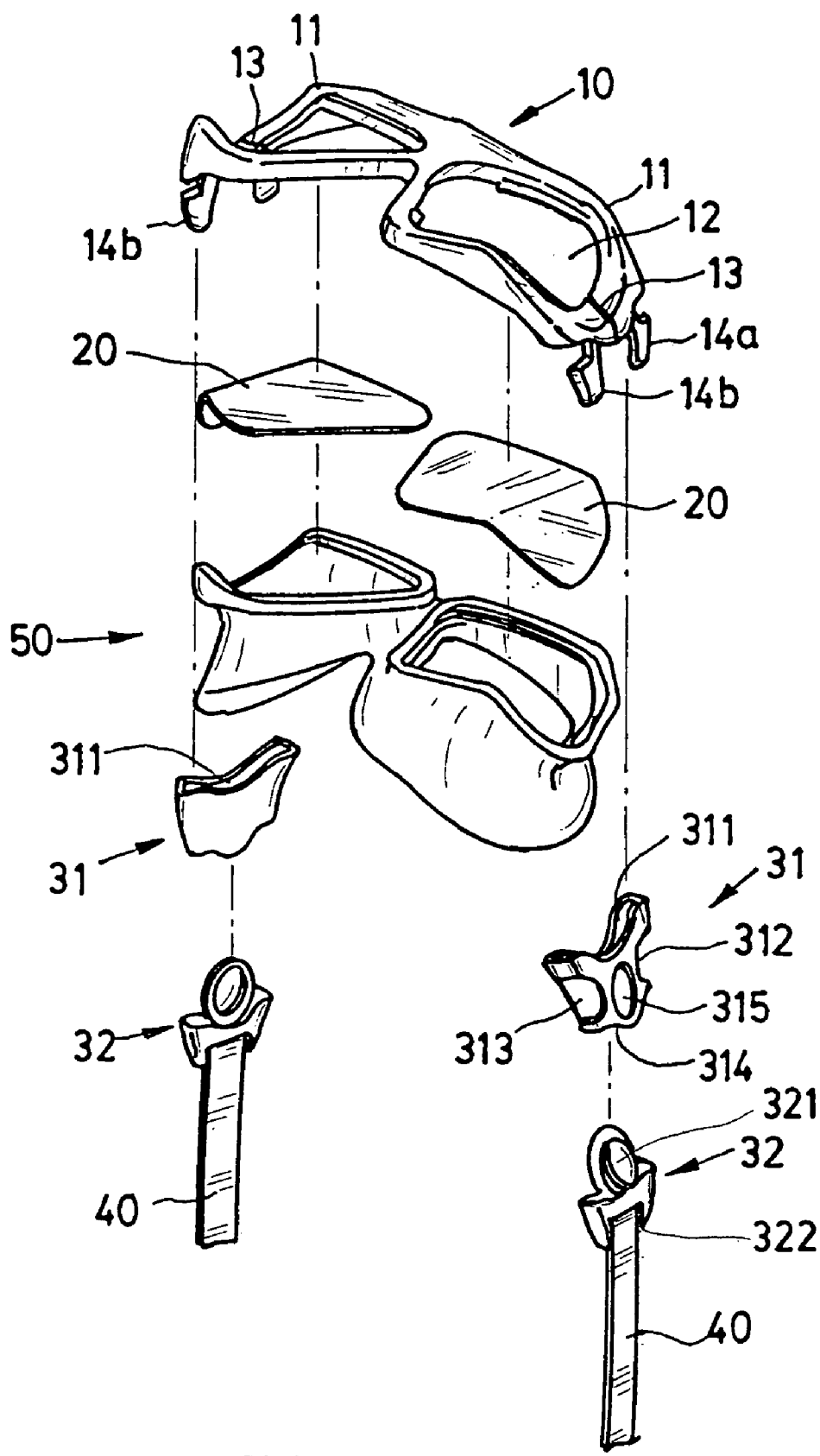
FIG. 4 is an exploded view of a second embodiment of goggles according to the present invention.
Figure 5:
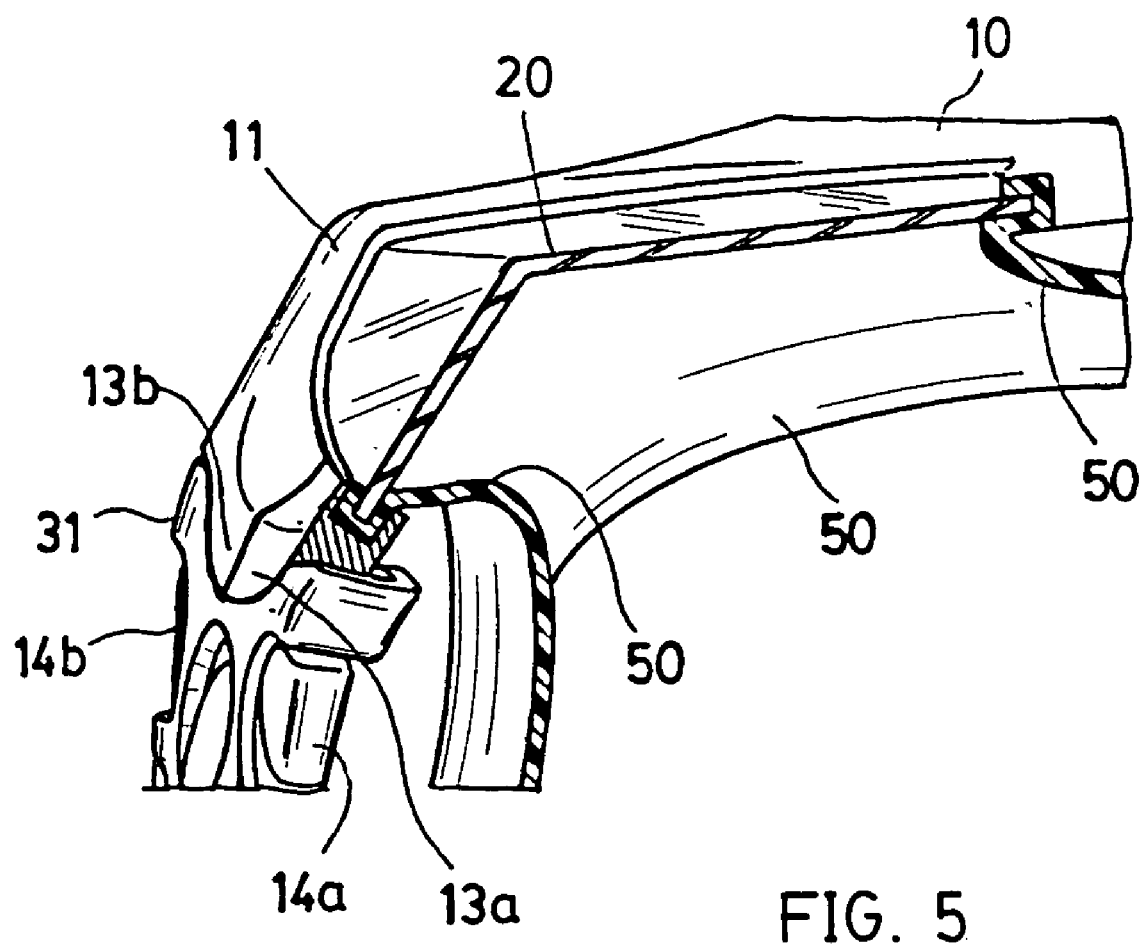
FIG. 5 is a sectional view of an endpiece of assembled goggles according to FIG. 4.

FIGS. 4 and 5 show a pair of goggles constructed in accordance with a second embodiment of the present invention. The second embodiment is substantially the same structure as the first embodiment. However, the second embodiment includes a flexible second frame 50. The flexible second frame 50 is connected together with the main frame 10 and the lenses 20. In the second embodiment, the lenses 20 can be inserted into the main frame 10 before being connected with the flexible second frame 50 or the lenses 20 can be inserted into the flexible second frame 50 before being connected with the main frame 10.

The second frame 50 is soft so that it will comfortably seal against a face of a user wearing the goggles.

The goggles of the present invention can be used as safety goggles, swimming goggles, ski goggles, or the like.

The disclosed embodiments of the present invention are only the preferred embodiments. Any minor changes or modifications partially or wholly to the present invention conducted by other professional and made publicly known or familiar shall be deemed to be derived from the present inventive concept and will be within the scope of the claims of the present invention.

What is claimed is:

1. A pair of goggles comprising:
   a) a main frame having:
      i) two fitting members, each of the two fitting members having upper and lower members movable between open and closed positions, in the closed position the upper member is located adjacent to the lower member, and in the open position the upper member and the lower member are spaced apart;
      ii) two lens openings, one of the two lens openings being located on an interior of each of the two fitting members; and
      iii) two latches, each of the two latches extending rearwardly from one of the two fitting members
   b) two lenses, each of the two lenses removably inserted into one of the two lens openings;
   c) two hollow side guards, each of the two hollow side guards being removably connected to one of the two latches; and
   d) a band adjustably secured to the side guards,
   wherein the lenses are removable when the upper and the lower members are in the open position and the lenses are fixed in the frame when the upper and the lower members are in the closed position, wherein each of the two latches includes an upper latched member connected to the upper member and a lower latched member connected to the lower member, each of the two hollow side guards includes a hollow forward member having a forward opening, two side openings, an outer opening, and a rear opening, the upper and lower latched members being inserted into the forward opening and protruding from the side openings.

2. The goggle according to claim 1, wherein each of the two hollow side guards includes a rear member having a forward projection and a rear slot, the rear member being inserted into the rear opening in the hollow forward member and the forward projection protruding from the outer opening, the band being adjustably connected to the slot at opposite ends thereof.

3. The goggles according to claim 1, further comprising a flexible second frame connected to the main frame.

4. The goggles according to claim 3, wherein the flexible second frame is located between the main frame and the lens.

* * * * *